United States Patent [19]

Knöfel et al.

[11] Patent Number: 5,663,424
[45] Date of Patent: Sep. 2, 1997

[54] FRACTIONATION AND PURIFICATION OF AROMATIC POLYAMINE MIXTURES AND THE USE THEREOF

[75] Inventors: Hartmut Knöfel, Odenthal; Michael Brockelt, Leverkusen, both of Germany

[73] Assignee: Bayer Aktiengesellschaft, Leverkusen, Germany

[21] Appl. No.: 623,239

[22] Filed: Mar. 28, 1996

[30] Foreign Application Priority Data

Apr. 7, 1995 [DE] Germany ............... 195 13 070.7

[51] Int. Cl.$^6$ ............................... C07C 209/86
[52] U.S. Cl. ............... 560/347; 564/315; 564/331; 564/332; 564/333; 564/334; 564/437; 564/450; 564/451
[58] Field of Search ............... 564/315, 331, 564/332, 333, 334, 437, 450, 451; 560/347

[56] References Cited

U.S. PATENT DOCUMENTS

| | | | |
|---|---|---|---|
| 4,087,459 | 5/1978 | Knöfel et al. | 564/331 |
| 4,914,236 | 4/1990 | Knöfel et al. | 564/334 |
| 4,924,028 | 5/1990 | Knöfel et al. | 564/331 |
| 5,196,591 | 3/1993 | Knöfel et al. | 564/331 |
| 5,359,141 | 10/1994 | Knöfel et al. | 564/331 |

FOREIGN PATENT DOCUMENTS

| | | |
|---|---|---|
| 2238319 | 2/1973 | Germany . |
| 1170619 | 11/1969 | United Kingdom . |

*Primary Examiner*—Richard L. Raymond
*Attorney, Agent, or Firm*—Joseph C. Gil

[57] ABSTRACT

The invention relates to a process for the fractionation and purification of aromatic polyamine mixtures and the use thereof.

9 Claims, 4 Drawing Sheets

FRACTIONATION AND PURIFICATION OF AROMATIC POLYAMINE MIXTURES AND THE USE THEREOF

BACKGROUND OF THE INVENTION

The present invention relates to a process for the fractionation and purification of aromatic polyamine mixtures and the use thereof.

The preparation of aromatic polyamines and polyamine mixtures, particularly of the diphenylmethane series, is described in numerous patent applications and patents, as is the use of said products. Outstanding importance is attached to the use of said products as raw materials for the preparation of isocyanates, usually by reaction of the polyamine mixtures with phosgene according to the generally conventional and well known methods.

In many cases, however, the resulting isocyanates and isocyanate mixtures are not obtained in the form and composition subsequently used in preference in the isocyanate stage but have to be converted beforehand to the appropriate form for use by means of, in some case, time-consuming work-up and separation processes. Suitable polyamine preliminary stages which may be converted in a less time-consuming manner to the isocyanate use forms are in many cases difficult to produce or unobtainable in terms of process technology, or economically unattractive.

An example is the production of 4,4'-diisocyanato-diphenylmethane which is important for the preparation of valuable polyurethane materials, the amine preliminary stage of which may be obtained usually from aniline and formaldehyde only together with isomers, particularly the 2,4'-isomers and polyamines with a relatively large number of functional groups. Although said constituents are the basis for the likewise sought after isocyanates, the separation of the crude isocyanates into the isocyanates and isocyanate mixtures suitable for subsequent use is not easy. Initially, a part of the binuclear compounds are usually separated from the remainder. The 4,4'-diisocyanato-diphenylmethane from the binuclear fraction is then separated from the other isomers in a second distillation stage requiring many separation stages.

Even in recent times, the 2,4'-isomer in the enriched form has gained increasing importance as a polyurethane raw material, but may be enriched compared with the 4,4'-isomer and separated from the 2,2-isomer possibly present only by an elaborate distillation procedure.

Isomer separation methods or enrichment methods within the fraction of polynuclear-homologues, or of polyfunctional amine constituents, and of isocyanates of the diphenylmethane series, are practically unknown.

4,4'-Diaminodiphenylmethane is also attracting increasing interest as a raw material for di-(4-isocyanato-cyclohexyl)methane, the form of 4,4'-diisocyanato-diphenylmethane hydrogenated on the nucleus, the provision of suitable aromatic polyamine mixtures for the hydrogenation stage with the highest possible content of 4,4'-diaminodiphenylmethane with simultaneously the smallest possible proportion of 2,4'-diaminodiphenylmethane being very expensive.

It is well-known that amines may be separated in certain cases by partial conversion to their salts, wherein the different base strengths inter alia may be used. These are usually monoamines with very different base strengths. Such disproportionation effects in two-phase systems have also been described already for aromatic polyamine mixtures, particularly of the diphenylmethane series (German Auslegeschriften 2,238,319 and 2,528,697).

As a result of the numerous components present in such a mixture, the amino groups of which hardly differ at all in terms of type practically all of them are arylamino groups—the effects are not particularly great and pronounced to be of interest for direct use with simple means.

The object of the present invention was to provide a process which allows aromatic polyamine mixtures to be fractionated and purified in a simple manner so that isomers are obtained in a pure or enriched form.

DESCRIPTION OF THE INVENTION

The above noted object is achieved by the process according to the invention which achieves a surprisingly good separating efficiency during the fractionation of aromatic polyamine mixtures, particularly of the diphenylmethane series, and in terms of its effect thereby far exceeds the known effects of the prior art.

Other polyamine mixtures of varying composition are obtained during the fractionation of aromatic polyamine mixtures according to the invention. The derived polyamine mixtures may be those that are obtainable only at great expense by known synthesis routes. They may also be polyamine mixtures which are more suitable for a simplified preparation of isocyanates than the well known polyamine mixtures that are technically easy to prepare in that they, e.g., anticipate in the amine stage the isomer separations that are difficult to perform in the isocyanate stage. Such mixtures may also be completely new polyamine mixtures, because they cannot be prepared according to the prior art, which lead to completely new types of isocyanates.

The process according to the invention may be used to obtain from any—thus including recycled—polyamine mixtures product fractions conforming with the standard or the starting polyamines despite the polyamine mixtures differing from the originally used polyamines or isocyanates in terms of contamination or non-random i.e. selective losses in the case of individual components.

Finally, the process according to the invention may be used to co-fractionate synthesis-dependent by-products and intermediates unwanted in the end product and to deplete them in one product fraction and enrich them accordingly in another, and optionally to expel them in an individual fraction.

The invention provides a process for the fractionation and purification of aromatic polyamine mixtures, particularly polyamine mixtures of the diphenylmethane series, which is characterized in that a) the polyamine staffing mixture (A) is distributed in a two-phase system comprising (i) a hydrophobic solvent phase (B) which is composed substantially of hydrophobic solvent and optionally an aromatic auxiliary amine that is practically insoluble in water and under normal pressure has a boiling point at least 20° below the boiling point of the lowest boiling component of the staffing mixture and at least 20° C. above the boiling point of the solvent, and optionally of polyamine, and (ii) an aqueous phase (C) comprising substantially water, a strong acid and auxiliary amine present at least partially in the salt form, and optionally polyamines present at least partially in the salt form, with the assistance of an extraction stage (4) operating on the counter-current principle with mixing of the phases, by introducing the starting polyamine mixture via the aqueous phase, into the extraction stage (4), and the organic phase (D) leaving the extraction stage (4) is separated b) optionally at least partially by means of an intermediate extraction stage (3) and/or c) optionally with separation of a partial stream before or after the extraction stage (3) optionally passed through, and return of the separated partial stream to the extraction stage (4) via an upstream extraction stage (2)

d) in a multi-stage distillation (6.1), (6.2) into a first fraction (E), composed substantially of hydrophobic solvent and optionally auxiliary amine, a second fraction (F) composed substantially of auxiliary amine and optionally hydrophobic solvent and a distillation residue (G) composed substantially of a first polyamine fraction, and e) the aqueous phase (H) leaving the extraction stage (4) is fed to an extraction stage (5) in which an extraction of the aqueous phase takes place according to the principle of counter-current extraction with a solvent phase (J) comprising a solvent and auxiliary amine, and the aqueous phase (K) depleted in polyarylamine results, which is returned f) optionally at least partially via an intermediate distillation stage (8)

g) optionally, at least partially via an intermediate extraction stage (3) and/or h) optionally at least partially, initially via an upstream extraction stage (2) and subsequently via an optionally present extraction stage (3)

i) to the extraction stage (4) where it is used again as stream (C), optionally after the addition of water and/or auxiliary amine, and j) the organic phase (L) obtained in the extraction stage (5) is split into a distillate (M) comprising hydrophobic solvent and auxiliary amine and a distillation residue (N) comprising a second polyamine fraction, after which the distillate (M) is combined with at least a partial quantity of the distillate (F) obtained in the second distillation stage (6.2) of the organic phase (D) and is subsequently returned to the extraction stage (5) where it is used again.

The numbers and capital letters noted-above and used in the description which follows refer to streams and elements in the drawings.

In preference, the process is carried out in such a way that f) before being re-used, the aqueous phase (K) leaving the extraction stage (5) is freed at least partially from a part (X) of the water contained therein by distillation (8), said water being used optionally for washing (6.0) that part of the organic phase (D) leaving the extraction stage (4) and/or of the organic phase (P) leaving the extraction stage (3) fed to work-up by distillation (6.1), (6.2), and/or for washing (7.0) that part of the organic phase (L) leaving the extraction stage (5) fed to work-up by distillation (7.1) for the purpose of removing acid traces, the water (Y) obtained in so doing is returned to the aqueous phase at a suitable place and the resulting concentrated aqueous phase is combined with the optionally remaining residue of (K) and re-used as stream (C).

The process according to the invention is carried out particularly preferably in such a way that b) the organic phase (D) obtained in the extraction stage (4) is extracted in counter-current at least partially in an intermediate extraction stage (3) with at least a partial quantity of stream (C) and/or is extracted in counter-current with at least a partial quantity of the aqueous phase obtained in the optionally present upstream extraction stage (2), the aqueous phase resulting in the intermediate extraction stage (3) is fed to the extraction stage (4) and the organic phase obtained in the intermediate extraction stage (3) is fed to the work-up stage (6).

A further improved and therefore preferred embodiment of the process according to the invention consists in that c) a partial stream of the organic phase (D) leaving the extraction stage (4) and/or partial stream of the organic phase leaving the optionally present intermediate extraction stage (3) is separated, and extracted in counter-current in an upstream extraction stage (2) with a partial quantity, preferably with the entire quantity of the aqueous phase available as stream (C), the organic stream used in the extraction stage (2) is metered such that the most extensive transfer possible of the polyamine contained in the above-mentioned organic stream to the aqueous phase takes place in (2), the aqueous phase resulting in the upstream extraction stage (2) is fed to the extraction stage (3) optionally after the addition of water from stream (Y) and/or auxiliary amine, and the organic phase (T) obtained in the upstream extraction stage (2) and depleted in polyamine is fed to the extraction stage (4).

More particularly, the present invention, in its broadest embodiment, is directed to a process for the fractionation and purification of aromatic polyamine mixtures, in particular of polyamine mixtures of the diphenylmethane series, comprising:

a) mixing the polyamine starting mixture (A) in a first extraction stage (4) with a two-phase system comprising (i) a hydrophobic solvent phase (B) which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase (C) consisting essentially of water, a strong acid and auxiliary amine present at least in part in the salt form, and optionally polyamines present at least in part in the salt form, with said first extraction stage (4) operating on the countercurrent principle, and wherein said polyamine starting mixture (A) is introduced into said first extraction stage with said aqueous phase (C), with a first aqueous phase (H) and a first organic phase (D) exiting said first extraction stage (4), b) distilling said first organic phase (D) in a multi-stage distillation (6.1), (6.2) into i) a first fraction (E) consisting essentially of hydrophobic solvent and optionally auxiliary amine, ii) a second fraction (F) consisting essentially of auxiliary amine and optionally hydrophobic solvent, and iii) a distillation residue (G) consisting essentially of a first polyamine fraction, c) extracting said first aqueous phase (H) in a second extraction stage (5) with a solvent phase (J) consisting essentially of hydrophobic solvent and auxiliary amine, said second extraction stage (5) operating on the countercurrent principle, with i) a second aqueous phase (K), said second aqueous phase (K) being reduced in amine content and ii) a second organic phase (L) exiting said second extraction stage (5), d) separating at least a portion of said second organic phase (L) in a distillation stage (7.1) into
   i) a first distillate (M) consisting essentially of hydrophobic solvent and auxiliary amine, and
   ii) a distillation residue (N) consisting essentially of a second polyamine fraction, e) recycling said second aqueous phase (K) as at least a portion of stream (C), and f) combining said first distillate (M) with a least a portion of said second fraction (F) to form at least a portion of solvent phase (J).

The auxiliary amine used is preferablyaniline and the polyamine mixture of the diphenylmethane series used is preferably a polyamine mixture of the kind obtained during acid-catalyses aniline-formaldehyde condensation.

The polyamine mixtures treated in this way, i.e. the fractions produced with the process according to the invention, are used for the preparation of the corresponding aromatic polyisocyanate mixtures and for the preparation of polyurethane plastics. Moreover, the fractions produced according to the process of the invention may be used for the preparation of the corresponding polyamines hydrogenated on the nucleus or as cross-linking agents and as epoxy curing agents. The corresponding polyisocyanates prepared from the fractionated polyamine mixtures are used preferably for the preparation of polyurethane foams.

Starting mixtures are, for example, technical-grade arylamine mixtures, of the kind obtained during preparation from the starting compounds or of the kind obtained during recovery. Examples of starting arylamine mixtures for the fractionation and purification of which the process according to the invention is particularly suitable are 1. Polyamine mixtures of the diphenylmethane series, of the kind produced during the condensation and acid-catalyses rearrangement of aniline with formaldehyde,
2. Polyamine mixtures of the diphenylmethane series, of the kind obtained during acid-catalyses condensation of substituted anilines with formaldehyde,
3. Polyamine mixtures of the diphenylmethane series, of the kind obtained during mixed condensation of substituted anilines with one another and/or aniline with formaldehyde,
4. Polyamine mixtures of the diphenylmethane series, of the kind obtained during the condensation, including mixed condensation, of substituted anilines and/or aniline with aldehydes and/or ketones,
5. Polyamine mixtures of the diphenylmethane series of the kind produced during the nitration and subsequent reduction of di- and/or polyarylmethanes and/or substituted di- and/or polyarylmethanes; the term polyarylmethanes here means in particular the benzyl homologues of diphenylmethane,
6. Polyamine mixtures of the diphenylmethane series, of the kind produced during the condensation of monoarylmonoamines (e.g. aniline, substituted anilines) and/or monoaryldiamines (phenylene diamines, substituted phenylene diamines) with aldehydes, ketones, particularly formaldehyde, and acid-catalyses rearrangement, and
7. Polyamine mixtures of the triphenylmethane series, of the kind produced, e.g. during the nitration and subsequent reduction of triphenylmethane, particularly alkyl-substituted triphenylmethanes and its polynuclear homologues, particularly benzyl homologues.

The hydrophobio solvents used are inert solvents with a boiling point in the range from 30° to 280° C., preferably from 80° to 200° C., such as, for example, chlorobenzene, dichlorobenzene, benzene, toluene, ethylbenzene, cumene, xylene, dichloroethane, chloroform and carbon tetrachloride. Xylenes i.e. technical-grade xylene mixtures, particularly oxylene, toluene, ethylbenzene, cumene and chlorobenzene, are used in preference. The preferred solvents are those having a good solvent power for the polyamine mixtures used.

The acids used are water-soluble protonic acids with a pKA value below 2.5, preferably below 1.5. Examples thereof are hydrochloric acid, hydrobromic acid, sulfuric acid, trifluoroacetic acid, methanesulphonic acid or phosphoric acid. Hydrochloric acid and methanesulphonic acid are preferably used. The acids mentioned may also be used in mixture with acid or neutral salts of such acids, such as, e.g. the corresponding ammonium salts or the corresponding alkali salts. The acids mentioned are not used in the free form but are present in the circuit system according to the invention in the form of the corresponding ammonium salts of the bases situated in the aqueous circuit system. They are generally polyamine mixtures of the kind of the starting mixtures and/or the auxiliary amines used.

Monoarylamines such as, e.g. aniline and/or aniline derivatives alkyl-substituted on the nucleus and/or on the nitrogen, are generally used as auxiliary amine. Primary anilines are used in preference; aniline is particularly preferred.

The process according to the invention may be carried out both batchwise and continuously. A preferred embodiment is the continuous method of operation. The process is carried out in all stages under the natural pressure of the system and preferably in an inert gas atmosphere (nitrogen).

The process according to the invention may be repeated with each of the resulting product fractions in order to increase the enrichment or corresponding depletion effect.

Figure 1:
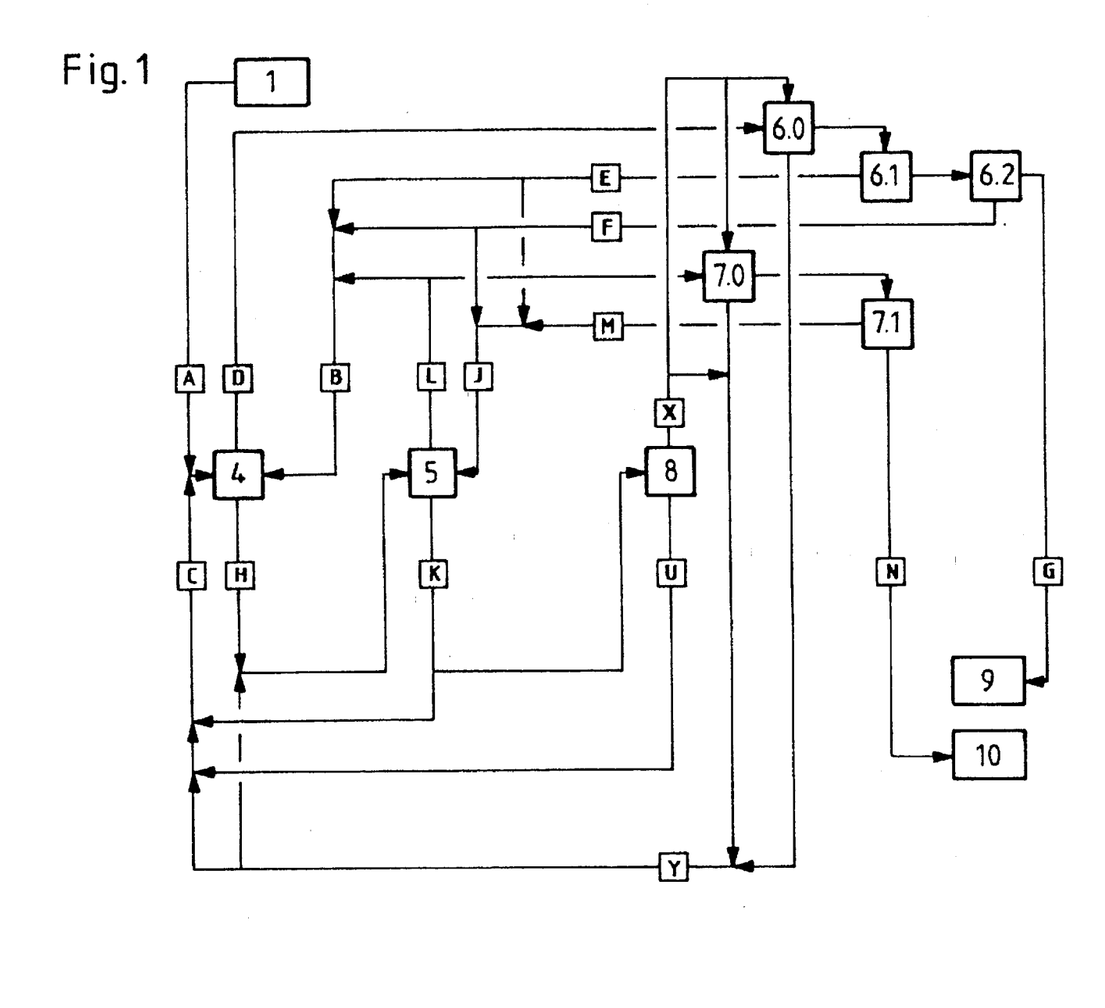
FIGS. 1 through 4 represent flow diagrams of embodiments of the present invention.
Figure 2:
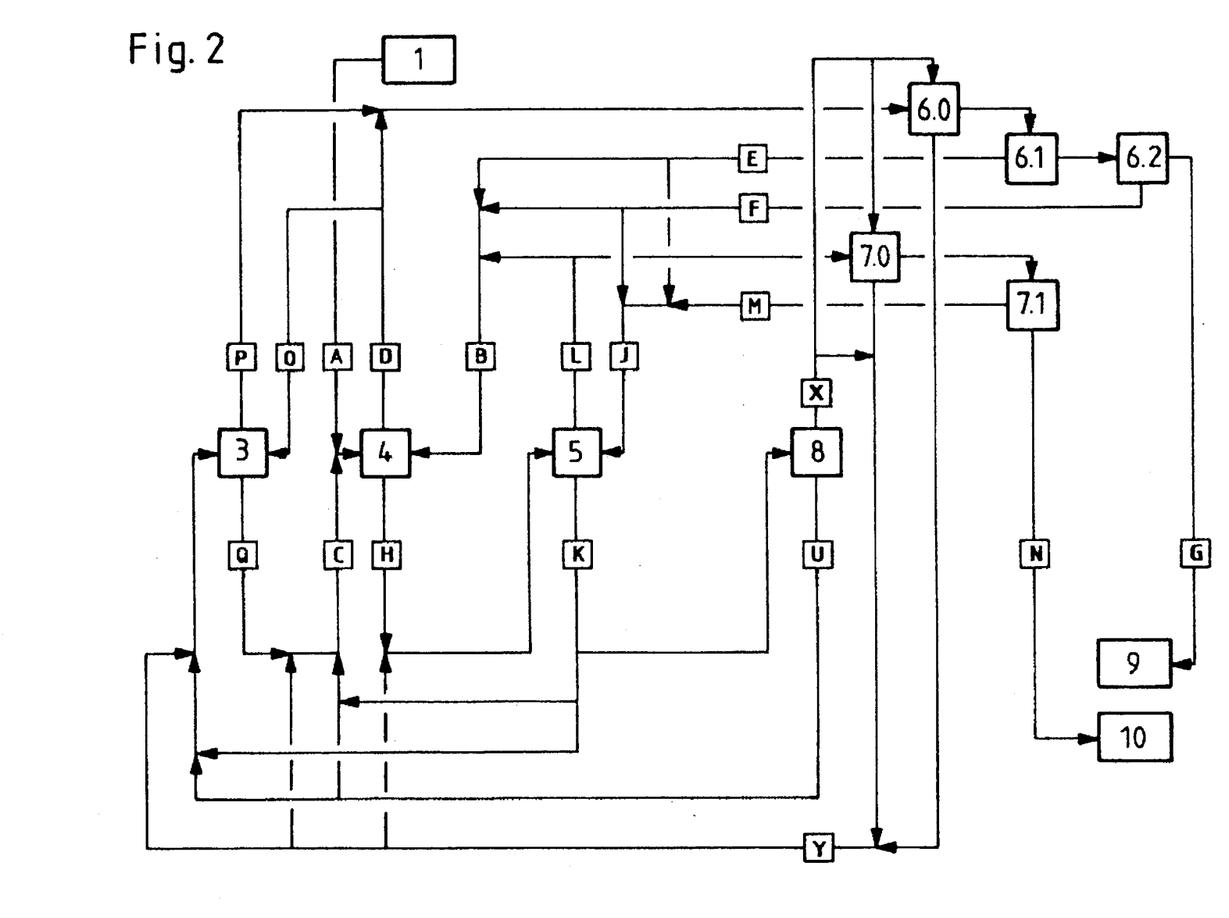
Figure 3:
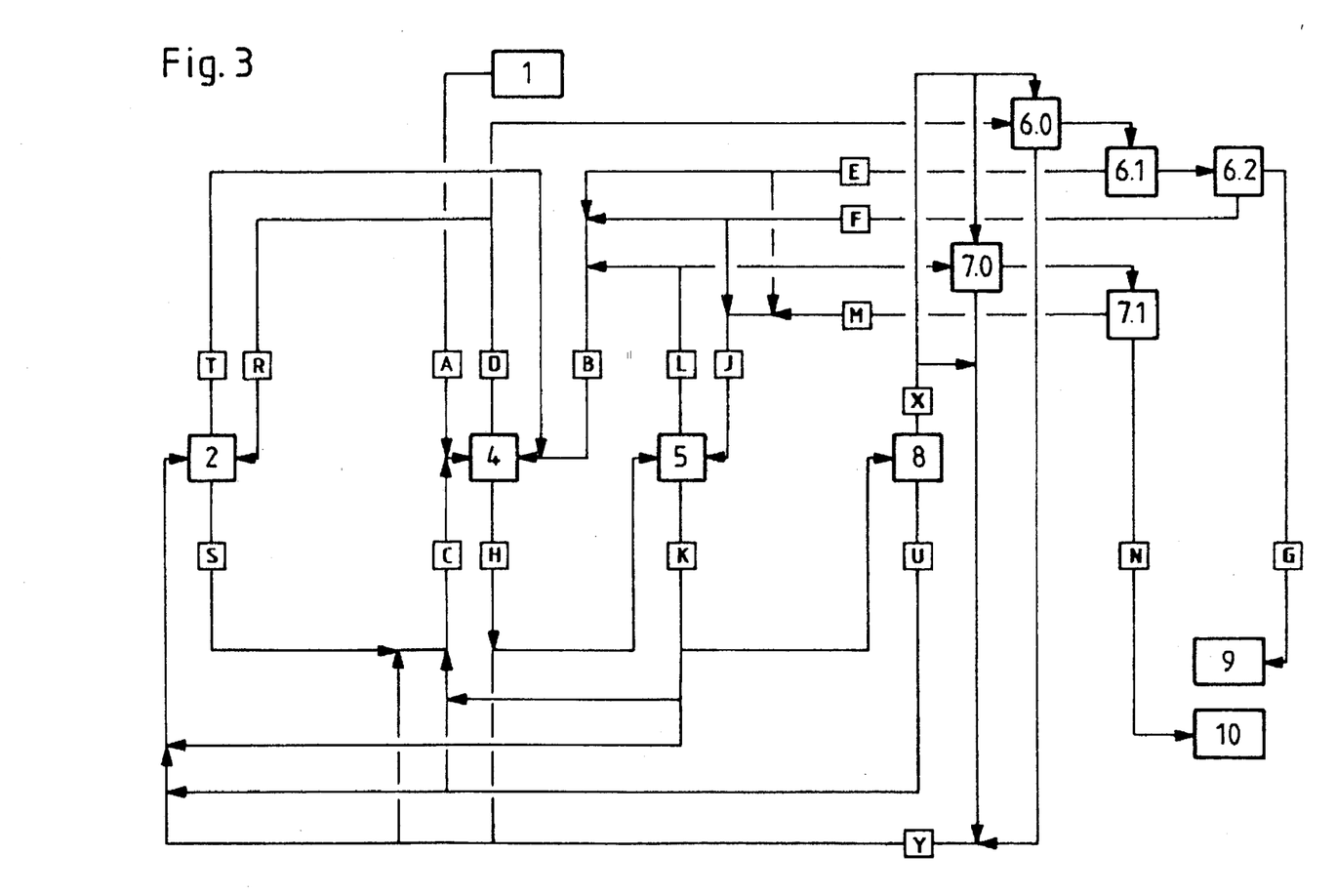
Figure 4:
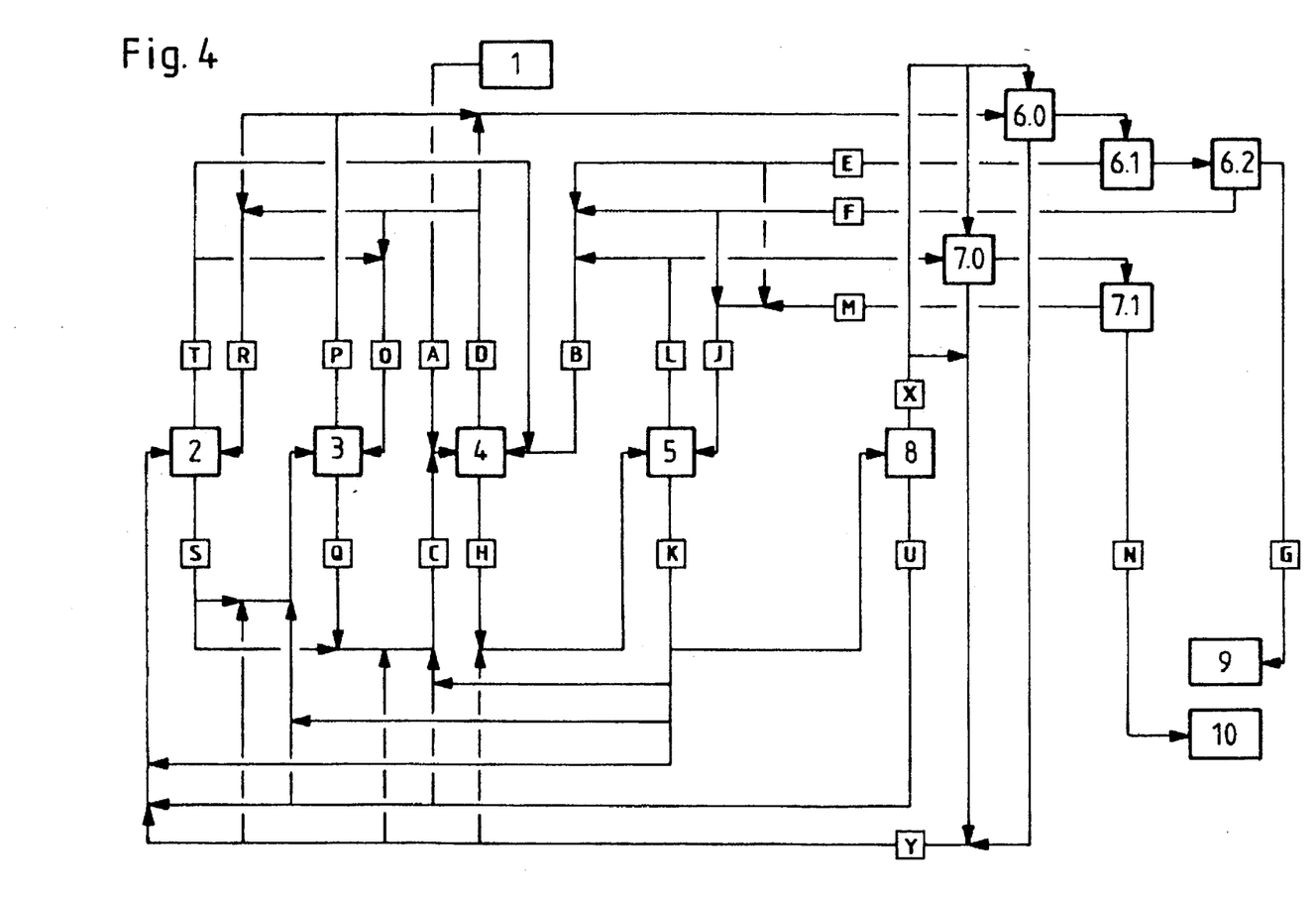

The process according to the invention may be carried out with two (FIG. 1), with three (FIG. 2 and FIG. 3) or with four (FIG. 4) extraction stages.

The flow diagrams shown in FIGS. 1 through 4 serve to explain the process according to the invention in more detail. The references in the figures have the following meanings:

(1) a tank for the starting arylamine mixture
(2) an upstream extraction stage
(3) a first extraction stage
(4) an (intermediate) second extraction stage
(5) a (final) third extraction stage
(6) a work-up stage comprising
   (6.0) a wash stage
   (6.1) a first distillation stage of a multi-stage distillation
   (6.2) a final distillation stage of a multi-stage distillation
(7) a further work-up stage comprising
   (7.0) a wash stage
   (7.1) a distillation stage
(8) a water evaporator
(9) a tank for process product
(10) a tank for a further process product The reference symbols A-U, X and Y denote the streams to which reference is made below and in the examples.

The upstream extraction stage (2) is designed preferably as a multi-stage extractor. In the simplest case, the optionally interposed extraction stage (3) is composed of a mixer-separator unit, but multi-stage extraction units are also used here in preference. In the simplest case, the extraction stage (4) is a single-stage mixer-separator unit, but multi-stage extraction units are used in preference.

The final extraction stage (5) is generally designed as a multi-stage extractor.

The work-up stages (6) and (7) serve to separate the polyamine fractions which are obtained as distillation residues and are isolated as process products (G) and (N) in the tanks (9) and (10), and for the recovery of the hydrophobic solvent used and of the auxiliary amine used as distillates.

It has proved expedient to remove adhering traces of acid from the organic phases (D) and (D') and (L) and (L') fed to the distillation stages by extraction with water in upstream wash stages (6.0) and (7.0) before their treatment by distillation.

The actual work-up stage (6) generally, comprises an at least two-stage multi-stage distillation of which the first stage (6.1) provides a hydrophobic solvent as distillate (E) from which polyamine has been removed and which is depleted in auxiliary amine in comparison with the inflow product (D) and (D') and/or (P) and (P'), and of which the final stage (6.2) provides a depleted auxiliary amine as distillate (F) in comparison with (D) and (D') and/or (P) and (P').

The complete separation of hydrophobic solvent and auxiliary amine by distillation is not necessary when carrying out the process according to the invention.

In addition, the first polyamine fraction of the starting mixture (A) contained in stream (D) and (D') and/or (P) and (P') is obtained as distillation bottom product (G) in the final distillation stage (6.2).

In the simplest case, the work-up stage (7) comprises a distillation column (7.1) which is designed such that an extensive separation of hydrophobic solvent and auxiliary amine jointly as distillate (M) from the polyamine fraction (N) contained in the inflow to (6) takes place by distillation.

Preferably, however, the work-up stage (7) of the process according to the invention is also designed as a multi-stage distillation on account of the improved use of energy.

The distillation stage (8) is a device with which water can be removed by distillation from the aqueous phase of the system or from a partial stream of the aqueous phase. Such a stage is not necessary in principle for carrying out the process according to the invention, but because of the resulting advantages the embodiments including a water distillation stage (8) are preferred.

The aqueous phase containing the acid is practically a closed circuit system, so the stage (8) may, in principle, be inserted in any position of said circuit system. The position of stage (8) following the extraction stage (5) and before entry to the extraction stage (4) is the most advantageous and therefore the preferred embodiment.

The quantity of water removed (X), optionally after being divided up into partial streams and the different use thereof, is returned to the system at a suitable location in the form of the stream (Y) as a whole or in partial streams, so that an extended and optionally branched inherently closed aqueous circuit system is produced.

The system also includes the wash stages (6.0) and/or (7.0). The latter are extraction stages operating in one or more stages on the counter-current principle. In wash stage (6.0), the organic phase (D) and (D') and/or (P) and (P') is freed from adhering traces of acid with a partial stream of (X), and in wash stage (7.0) the organic phase (L) and (L') is freed from adhering traces of acid with the use of another water partial stream of (X).

The distillate (X) contaminated with hydrophobic solvent and auxiliary amine is highly suitable for wash stages (6.0) and (7.0). The resulting wash waters generally have a very much lower acid concentration than the actual acid circuit, so these may be recycled without difficulty in the form of stream (Y) or its partial streams; optionally, a partial quantity of distillate of (X) may be fed from (8) past the wash stages after (Y) and used to control the varying water content of the aqueous phase in the individual extraction stages.

The practically quantitative circuit operation of the acid used allows the use of expensive acids such as e.g. methanesulphonic acid which in turn, because of its reduced corrosion tendency, permits the use of inexpensive materials in the apparatus of the process according to the invention.

It has proved advantageous to define the acid content of the aqueous phase, independently of the varying amine content occurring in the aqueous phase of a two-phase system, by means of a so-called "molarity".

The "molarity" is defined as the theoretical concentration of 100% protonated amine (i.e. same number of acid and amine equivalents) in a volume of aqueous phase reduced mathematically by the proportion of unprotonated amine according to the formula:

$$\text{"molarity"} = \frac{\text{mol 100\% protonated amine}}{\text{vol. of aqueous phase} - \text{vol. of unprotonated amine}}$$

The molarity thus defined may assume values of up to 6 and is varied in a controlled manner in this range depending on the—product-related in this case—separation task on which the relevant embodiment is based.

It may also be advantageous within an embodiment of the process according to the invention to operate the individual process stages through which the aqueous phase passes, particularly the extraction stages (2) to (5), with a different molarity in the aqueous phase by withdrawing or adding water from or to the aqueous phase between the individual stages.

The upper limit of said operating range is technically limited on the one hand by the increasing crystallization tendency of the amine salts with increasing concentration, particularly at high degrees of protonation, and on the other hand by the increasing mutual solubility of the phases in one another, particularly at low degrees of protonation. The degree of protonation represents the ratio of acid equivalents to amine equivalents. The lower limit of said range is limited by economic factors by the decreasing acid content and hence the quantitative decrease in the separating efficiency, i.e. for an outstanding qualitative separating efficiency and without technical difficulties, an increasingly large volume of aqueous phase is required for the separation of a given quantity of amine as the molarity falls.

According to one variant of the process of the invention, the feeding of the starting polyamine mixture (A) from the storage vessel (1) takes place by mixing with the partial stream (C) and introduction of the mixture into the extraction stage (4).

The stream (C) is generally composed of water, a strong protonic acid, auxiliary amine and optionally polyamine. The acid is present in the form of its salts dissolved in water with auxiliary amine and optionally with polyamine. The amino groups of auxiliary amine and optionally polyamine are always present in (C) in a stoichiometric excess, based on the acid.

The degree of protonation in (C) is generally 10–90%, for the aniline used preferably as auxiliary amine it is preferably 25–70%.

The well-defined molarity of stream (C) measured and controlled in narrow limits for the relevant embodiment of the process according to the invention is varied in a controlled manner in a wide range depending on the—product-related in this case -separation task on which the relevant embodiment is based. Generally, the aqueous phase fed to the extraction stage (4) of the process according to the invention has a molarity of between 0.5 and 6.

In extractor (4), stream (B) is passed in counter-current to the mixture produced from (A) and (C).

The organic phase (B) is generally composed of auxiliary amine and/or polyamine, in addition to hydrophobic solvent, the latter polyamine preferably having the composition of the second process partial product (N).

if an organic phase (B) without polyamine is used, a polyamine fraction is obtained in the aqueous phase (H) leaving the extraction stage (4), in which fraction the relative enrichment of the components contained in preference in said phase may be increased selectively and maximized at the expense of the polyamine concentration in the aqueous phase.

The effect of polyamine as a constituent of the organic phase (B) is that the phase (H) leaving the process stage (4) has a polyamine concentration that is higher and hence more advantageous in energy terms for carrying out the process of the invention than when an organic phase (B) without polyamine is used.

As a result of the preferred use of a polyamine with the composition of the second partial product (N) as constituent of the organic phase (B), the relative enrichment of the polyamine components contained in preference in the aqueous phase (H) leaving the separation stage (4) and hence of the second polyamine fraction (N) may be varied and maximized at a higher and hence more advantageous concentration level due to equilibrium adjustment with self-intensification of the separating effect.

In the simplest case, stream (B) is formed from the hydrophobic solvent from which polyarylamine (G) has been removed and which is depleted in auxiliary amines, and which is obtained as distillate stream (E) in the distillation stage (6.1) and to which is added optionally a partial quantity of the distillate stream (F) of distillation stage (6.2) from which polyamine (G) has been removed and which is depleted in hydrophobic solvent.

In a preferred embodiment, at least a partial quantity of the distillate stream (E) and optionally at least a corresponding additional partial quantity of the distillate stream (F) is added to the stream (J) used as extraction agent in the final extraction stage (5) and, after passing through stage (5), removed as a partial quantity from the resulting organic phase (L) and added to the stream (B).

Optionally, in a particularly favorable but not generally applicable embodiment, the total quantity of streams (E) and (F) are added to the stream (J) and used initially as extraction agent in extraction stage (5) so that the stream (B) is formed exclusively from a partial quantity of the stream (L) leaving the extraction stage (5).

The aromatic amine content of the organic phase (B) is usually 15–60%, depending on the separating task.

In the extraction stage (4) operated preferably in multiple stages, the organic phase (B) and the mixture of starting polyamine mixture and aqueous phase (C) are fed in counter-current with intimate mixing.

A partial transfer of polyamine to the organic phase usually takes place during this process, optionally in exchange for auxiliary amine in the opposite direction.

The starting polyamine (A) introduced into the extractor (4) together with the aqueous phase (C) is divided into the aqueous phase (H) leaving the extractor and the organic phase (D) leaving the extractor (4) (quantitative fractionation).

The quantitative division of the individual components of the starting polyamine mixture into the resulting aqueous phase (H) and the resulting organic phase (D) takes place under the conditions of the process of the invention with a surprisingly high selectivity such that the resulting product fractions have a different composition which, in certain circumstances, differs considerably from that of the starting polyamine mixture (qualitative fractionation).

For example, starting from the aniline formaldehyde condensation products used in preference, it was found that the ortho-isomer form(s) of the polyamine component contained in two or more isomer forms in the starting mixture is (are) usually relatively enriched in the organic phase (D) leaving the separating stage (4); for example, 2,4'-diaminodiphenylmethane relative to 4,4'-diaminodiphenylmethane. Conversely, the resulting aqueous phase (H) is relatively depleted in the 2,4'-isomer, whilst the 4,4'-isomer is relatively enriched.

If several "ortho-isomers" are present in the starting polyamine, e.g. 2,2'- and 2,4'-diamino-diphenylmethane, then the "ortho-richer" 2,2'-isomer is more greatly enriched in the organic phase (D) compared with the "ortho-poorer" 2,4'-isomer, that latter itself being relatively enriched compared with the "even ortho-poorer" 4,4'-isomer.

The enrichment and depletion effect found initially with the aniline formaldehyde condensation products of the diaminodiphenylmethane series was associated on a purely empirical-descriptive basis with the criterion of ortho and para substitution. The derived characterization of the process products as "ortho-rich" and "ortho-poor" is relative, and was expressed by the term "degree of ortho-substitution".

The "degree of ortho-substitution" is defined as the ratio of ortho amino group to methylene group relationships to the total number of all the amino group relationships. This term can cover practically all the isomer separations for polyamines which are produced from arylamines, including substituted arylamines, with carbonyl compounds in an aqueous acid medium.

Surprisingly, the same enrichment-depletion effect—classified according to degree of ortho-substitution—was also found for the well-characterized and analytically detectable isomeric trinuclear compounds from aniline-formaldehyde condensation.

The same applies to the separation of condensation products from formaldehyde with aniline and diaminoaryl compounds such as phenylene or alkyl-substituted phenylene diamines.

The polyamine mixtures mentioned hitherto, as a result of their preparation, possess amino groups which are practically only in the ortho and/or para position to methylene groups.

Within one group of isomeric compounds, those with the higher degree of ortho substitution are usually enriched in the organic phase (D) during fractionation compared with the isomers with a lower degree of ortho substitution.

Polyamine mixtures particularly of the diphenylmethane series including the relevant polynuclear homologues which are prepared according to other processes, for example, by nitration of diphenylmethane or methyldiphenylmethanes and subsequent reduction possess, in addition to amino groups in the ortho and para positions, other amino group-methylene group relationships as a result of the preparation. The process according to the invention is equally effective for said polyamine mixtures.

For example, a polyamine mixture which primarily represents an isomer mixture of and can be prepared from a mixture of 2- and 4-methyldiphenylmethane by nitration and subsequent reduction.

During the fractionation of such mixtures by means of the process of the invention, the 3,2'-isomers in the organic phase (D) are enriched compared with the 3,4'-isomers.

The criterion "ortho-rich" and "ortho-poor" or the degree of ortho-substitution in said polyamine mixtures no longer covers all the isomers and should therefore be applied mutatis mutandis in that, instead of the terms "in the ortho position" and "in the para position", the isomers are classified into those with a smaller (=ortho) and those with a larger (=para) spatial distance of the amino groups—usually situated on different six-membered rings—to the methylene bridge or of the amino groups to one another.

A further class of aromatic polyamine mixtures which can be fractionated very effectively by means of the process according to the invention are the polyamines of triphenylmethane and its polynuclear homologues, preferably benzyl homologues, of the kind produced, e.g. by nitration and subsequent reduction of the corresponding hydrocarbon mixtures.

During the fractionation of technical-grade polyamine mixtures of the last classes of substance mentioned I. Mixed condensation products of mono- and diaminoaryl compounds with formaldehyde and general carbonyl compounds, II. Polyamine mixtures from processes by nitration and subsequent reduction of diphenylmethane and preferably substituted, particularly alkyl-substituted, diphenylmethanes and the relevant homologues, and III. Polyamine mixtures from processes by nitration and subsequent reduction of triphenylmethane and preferably substituted, particularly alkyl-substituted, triphenylmethanes and the relevant polynuclear benzyl homologues a further surprising selectivity was found in addition to the pure isomer separation.

Polyamine mixtures of the substance classes I to III mentioned contain or may contain components in which at least one aryl nucleus per molecule beam more than one and usually two amino groups. Said components may be the preferred components of the polyamine mixture without having to be the main products in quantitative terms, due to the process.

In order to improve the characterization of such components, the term "degree of amino substitution" is used with which primarily the number of amino groups of one component in relation to the number of aryl nuclei is characterized. For aniline and its condensation products with formaldehyde, this expression is always 1.0, for phenylene diamine and its condensation products always 2.0. For pure mixed condensates, the value of 1.5 is obtained for the diphenylmethane isomers and values of between >1.0 and <2.0 are obtained for the polynuclear homologues. If the term degree of amino substitution is used statistically to characterize technical-grade polyamine mixtures, values of between 1.0 and 2.0 are likewise obtained.

When fractionating polyamine mixtures with a degree of amino substitution of >1.0 it was found that the components with a higher degree of amino substitution are relatively enriched in the aqueous phase resulting in the actual separation stage, the enrichment being greater with increasing degree of amino substitution.

The process according to the invention thus also opens up the possibility for this class of substances of divorcing the production form of the raw materials (amine stage) and the use form of the end products (isocyanate stage) so that a separate optimization of both stages is facilitated to the extent of obtaining completely new isocyanate mixtures.

These "achievements" are supplemented by a further criterion of selectivity which was found during the fractionation of technical-grade polyamine mixtures, particularly those with polynuclear homologues, and relates to the "nuclearity" of the polyamine mixtures.

The term "nuclearity" primarily expresses the number of aryl units of a component of an aromatic polyamine mixture. In the wider sense, the term nuclearity is used to express statistically a nuclearity of the total mixture for a polyamine mixture composed of numerous components with an individual, exact nuclearity.

Particularly surprisingly, it was found when fractionating polyamine mixtures with polynuclear components, particularly when fractionating technical-grade mixtures of aniline-formaldehyde condensates, that the polynuclear components in the organic phase leaving the fractionation stage can be both relatively enriched and relatively depleted in a controlled manner, depending on the molarity of the aqueous phase in the extraction stage (4).

A high molarity of the aqueous phase in (4) within the given molarity range leads to a relative depletion of polynuclear components in the organic phase (D) and consequently to a relative enrichment in the aqueous phase (H). A low molarity of the aqueous phase in (4) within the given molarity range leads to a relative enrichment of polynuclear components in the organic phase (D).

The surprising finding may be extended and refined to the extent that the relative enrichment and depletion also takes place amongst the polynuclear homologues themselves. In a technical-grade mixture of diaminodiphenylmethane, for example, if the trinuclear components in one fraction are relatively enriched or depleted compared with the binuclear components, a relative enrichment or depletion of tetranuclear components compared with trinuclear components is also found, i.e. an even greater relative enrichment or depletion, and the same occurs with pentanuclear components compared with tetranuclear components etc.

As a result of this and the isomer separation taking place simultaneously and always in the direction of a relative increase in the "degree of ortho-substitution" in the organic phase (D), and as a result of the possibility of repeating the separation according to the invention with individual product fractions, optionally with modified process parameters, there are numerous possibilities starting from well known and readily obtainable polyamine mixtures, of obtaining by means of the process of the invention less readily obtainable or completely new, because hitherto unobtainable by the prior art, polyamines and hence polyisocyanates. This is particularly true of products of the diamino- and diisocyanatodiphenylmethane series and quite particularly for polyamine and polyisocyanate mixtures with an extremely high proportion of polynuclear components.

The enrichment and depletion usually becomes more effective with increasing degree of protonation in the aqueous phase of the separation stage.

Moreover, the process according to the invention also proves to be generally effective for other polyamines with a similar structure. For example, the polyamine mixtures already mentioned which are obtained by nitration of di- and polyarylmethanes and subsequent reduction may also contain monoaminopolyaryl methane compounds or components in which one or more methylene groups have been converted by side-reactions into keto- and/or hydroxymethylene groups and thus into unwanted byproducts.

Numerous incompletely rearranged intermediate compounds and by-products may occur during the condensation of arylamines with carbonyl compounds. Most of these compounds usually undergo enrichment in one of the resulting fractions during the fractionation of the polyamine mixtures containing them, so that the effect can be used for separation and fractionation.

Such products may be optionally enriched in this way or may themselves be fractionated as selectively produced polyamine mixtures, such as, for example, polyaminobenzophenones or aminobenzylarylamine mixtures.

The organic phase (D) leaving the extraction stage (4) contains, inter alia, small quantities of acid, generally and depending on the process parameters in the extraction stage (4) between 0.01 and 0.5 wt. %, which are removed advantageously prior to work-up of the stream (D) by distillation.

In the simplest case, this takes place by neutralization with excess dilute aqueous bases, for example, dilute sodium hydroxide solution. The washing out of the acid or its amine salts from the organic phase with water is, however, preferred so that optionally only residual traces are removed by contact with dilute sodium hydroxide solution or by means of an ion exchanger.

The wash water used is removed from the aqueous acid circuit by means of a water evaporator and added thereto at a suitable location in process terms after passing through the wash stage(s) together with the acid.

The organic phase (D) is transferred to the at least two-stage distillation stage (6.1), (6.2), optionally after passing through the acid wash stage (6.0).

In the first distillation stage (6.1), a distillate (E) is separated which contains the majority, preferably almost the entire quantity of the hydrophobic solvent contained in (D) in addition to a part of the auxiliary amine contained in (D). Generally, the distillate (E) contains <50% of auxiliary amine, preferably 15–30%.

In the final distillation stage (6.2), the remaining auxiliary amine, optionally in addition to the residual quantity of hydrophobic solvent, is separated as distillate (F) from the first partial product (G) obtained as distillation bottom product and collected in the process product tank (9). Generally, (F) contains <50% of hydrophobic solvent, preferably 15–30%.

The corresponding second process partial product is situated in the aqueous phase (H) leaving the extraction stage (4). In a multi-stage extraction stage (5) operated preferably at 80°–110° C., the second partial product is extracted in exchange for auxiliary amine from the aqueous phase (H), optionally after the addition of water to reduce the molarity and optionally after the addition of auxiliary amine to reduce the degree of protonation, and in so doing is transferred to the organic phase (L).

The molarity of the aqueous phase used in (5) is preferably <2.5, while the degree of protonation of the aqueous phase used in (5) is preferably <60%.

The extraction agent (J) used is a mixture of hydrophobic solvent and auxiliary amine, which is composed substantially of the distillate fraction (M) of the distillation stage (7.1) and at least a partial quantity of the distillate fraction (F) of the distillation stage (6.2), and is optionally supplemented by at least a partial quantity of the distillate stream (E).

The weight ratio of auxiliary amine to solvent in (J) is generally between 0.5:1 and 3:1, preferably between 1:1 and 2:1.

The weight ratio of extraction agent (J) to aqueous phase is generally between 0.3:1 and 3:1, preferably between 0.7:1 and 2:1.

The organic phase (L) resulting in (5) or the partial quantity thereof is fed to the distillation stage (7.1), optionally after passing through the wash stage (7.0) and/or optionally after removal of acid traces with dilute sodium hydroxide solution.

The separation by distillation of the distillation residue (N) takes place in distillation stage (7.1), which residue is collected as a second partial product in the process product tank (10).

Distillation stage (7.1) may comprise, for example, a single-stage evaporator which provides a distillate (M) in addition to the distillation residue (N).

The distillate (M) contains, in addition to auxiliary amine, the entire hydrophobic solvent from (L) or the partial quantity thereof, and is used as extraction agent (J) after addition of at least a partial quantity of (F). For the general case that (F) contains hydrophobic solvent in addition to auxiliary amine, a corresponding equalization of hydrophobic solvent with respect to (E) is carried out if necessary, i.e. to the organic circuit in order to obtain the first partial product.

The aqueous phase (K) resulting in (5) is returned to the extraction stage (4), preferably at least partially via a distillation stage (8), in which the water quantity (X) is removed from the aqueous phase.

The route via (8) is absolutely vital if the extraction stage (4) is operated with a higher molarity of the aqueous phase than the extraction stage (5). In this case, the at least proportional return feed of water (Y) to the aqueous acid circuit takes place after leaving the stage (4) and before entering the stage (5).

In principle, the aqueous phase (H) resulting in the process stage (4) may be fed directly to the extraction stage (5). As, however, the upper molarity range of the extraction stage (4) much preferred for certain separation tasks lies above the preferred molarity range of the extraction stage (5), a preferred embodiment of the process of the invention is to divorce the molarities from those in the various extraction stages by removing water by distillation from the inherently closed system of the aqueous phase, optionally at a suitable location, and adding it again at another suitable location.

With the aid of a water distillation stage (8), water is removed from the aqueous phase containing the acid, or from a partial stream of the aqueous phase, preferably after leaving the extraction stage (5) and before re-use at the beginning of the process, said water being added again as a whole (Y) or in partial quantities at one or more locations before the aqueous phase enters the extraction stage (5).

A second variant of the process according to the invention is more advantageous and preferred as an embodiment, in which, additionally in the first polyamine fraction (G), the relevant enrichment of the components contained preferably in said fraction can be increased substantially and varied in a controlled manner, by extracting the organic phase (D) obtained in the extraction stage (4) at least partially in an intermediate extraction stage (3) from the viewpoint of phase (D) with an aqueous phase which comprises in the present case of variant 2 substantially at least a partial quantity of the stream (C).

For formal reasons, the organic phase fed to the extraction stage (3) is called stream (O), even if, as explained by way of example in the present case, it corresponds optionally at least in terms of composition but also preferably in terms of quantity with stream (D).

Even during the single-stage execution of the extraction stage (3), for example as a mixer-separator unit, a pronounced further relative enrichment of the components already enriched in (D) compared with starting polyamine (A) takes place in the resulting organic phase (P) depending on the type and, in particular, the quantity of aqueous phase used, associated with a decrease in the polyamine content in the organic phase (P). In view of the better effectiveness, however, the intermediate extraction stage (3) is preferably designed as a multi-stage extractor operated in counter-current.

The aqueous phase (Q) obtained in the extraction stage (3) contains the other corresponding fraction of the polyamine introduced with stream (O) in which fraction the components enriched in (P) are depleted accordingly. The extent of the relative depletion, i.e. the composition of the polyamine contained in (Q) is controlled under the relevant process conditions of the multi-stage extraction stage (3) by the qualitative and quantitative distribution equilibrium between the organic phase (O) fed in and the aqueous phase (Q) discharged.

The molarity of the aqueous phase in the extraction stage (3) is higher or the same or lower, depending on the separation task, based on the molarity in the downstream extraction stage (4) from the viewpoint of the aqueous phase, and is controlled by the addition or removal of water at a suitable location.

The aqueous phase (Q) resulting in process stage (3) is fed together with the optionally present remainder of (C) to the extraction stage (4), optionally after the addition of water.

The organic phase (P) resulting in stage (3) is fed together with the optionally present remainder of (D) to the work-up stage (6) in order to obtain the polyamine fraction (G).

With the second variant of the process according to the invention, the relative enrichment in both resulting polyamine fractions can be varied in a controlled manner and maximized. In addition to this great versatility and efficiency in terms of quality, the second process variant also offers a favorable embodiment from an energy viewpoint, at least for the second polyamine fraction (N).

The expenditure of energy associated with obtaining the first polyamine fraction (G) on the other hand increases more sharply in relative terms the lower the quantitative proportion of (G), based on the polyamine mixture (A) used, because the remaining polyamine content (G) in the organic phase (D) and (P) to be worked up by distillation optionally becomes increasingly small.

The effect is brought to bear in particular when the components separated with (G) are contained in the starting mixture (A) only in a small concentration and/or are enriched to a relatively high degree in the fraction (G), e.g. during the separation according to the invention of polyamine mixtures of the diphenylmethane series.

An improved embodiment in this respect is the third variant of the process according to the invention. Starting from the first variant, this is extended to the extent that the organic phase (D) leaving the process stage (4) is divided into a partial stream which is fed to work-up stage (6) with the further aim of obtaining the polyamine fraction (G), and a second partial stream which is fed to an upstream extraction stage (2).

For formal reasons, the organic phase fed to the upstream extraction stage (2) is called stream (R), even if, as explained by way of example in the present case, it corresponds optionally in terms of composition with stream (D).

Extraction stage (2) is usually a multi-stage extractor operated in counter-current in which the organic phase (R) fed in is extracted with at least a partial quantity, preferably with the total quantity of the aqueous phase (C) available for re-use.

The stream (R) fed to extractor (2) is metered such that, during the reaction with stream (C), the most extensive possible and preferably practically quantitative transfer of the polyamines contained in the organic phase (R) to the aqueous phase (S) leaving the extractor (2) takes place.

A higher molarity in the aqueous phase used in stage (2) resulting from process stage (8) of the process of the invention promotes and facilitates the transfer of polyamines from the organic phase (R) to the aqueous phase.

The residual polyamine content in the organic phase (T) resulting in the process stage (2) is generally <5 wt. %, preferably <1 wt. %. Moreover, the permissible maximum amine content in (T) and particularly the polyamine content depends on the qualitative requirements in respect of the process products resulting from the relevant separation task, and in the case of variant 3 particularly in respect of the process partial product (N). Maintaining the relevant polyamine content for the quality of (N) is controlled within the scope of the industrial conditions by metering the partial stream (R) whilst exhausting the aqueous phase available.

It is useful to the process and particularly to the extraction stage (2) that the greater the proportion of the second polyamine fraction (N) and consequently the smaller the proportion of the first polyamine fraction (G), the greater the aqueous phase (stream C) available for use in stage (2). A small polyamine fraction (G) usually means a low polyamine concentration in the organic phase (D) and a large expenditure of energy during work-up of such a phase. As a result of variant 3 according to the invention, the expenditure of energy in particular during isolation of the first polyamine fraction (G) can be reduced compared with variant 1.

The contribution of process stage (2) within the scope of variant 3 towards improving the process according to the invention lies in the fact that, instead of the total stream with a relatively low and hence unfavorable polyamine concentration in energy terms, only a partial stream with a correspondingly increased and hence more favorable concentration in energy terms is obtained for the work-up by distillation (6) to obtain the first polyamine fraction (G), (quantitative enrichment), whilst an organic phase (T) which can be used as extraction agent at a suitable location is obtained from the other partial stream without distillation.

The organic phase (T) largely free from polyamine leaving process stage (2) is fed to the extraction stage (4).

In the preferably multi-stage extraction stage (4), the organic phase (T) is added as extraction agent, usually by mixing with stream (B) and addition to the first stage of the extractor from the viewpoint of the organic phase (B).

Depending on an optionally present residual polyamine content in (T) and taking account of the quality of the second polyamine fraction (N), the organic phase (T) is added optionally to a later stage, from the viewpoint of the organic phase (B), optionally to the final stage of the multi-stage extraction stage (4).

The aqueous phase (S) leaving the process stage (2) contains, in addition to the acid present in the form of its ammonium salt, auxiliary amine and polyamine, the latter with a composition that largely corresponds to the polyamine in the organic phase (R) fed in.

In the case of variant 3 of the process according to the invention, the stream (S) is fed directly to the process stage (4), optionally after the addition of water from stream (Y) and/or further aqueous phase from stream (C).

As the polyamine fraction contained in the aqueous phase (S) usually has a higher relative (qualitative) enrichment in the direction of the first polyamine fraction (G) based on the starting polyamine (A), the result for the aqueous phase fed to extraction stage (4) after the addition of starting polyamine (A) is an "enriched" mixed polyamine compared with said starting polyamine, depending on the quantity ratio. As a result of the distribution equilibrium between the aqueous phase fed in and resulting organic phase (D), a limited qualitative enrichment effect for the first polyamine fraction (G) is also obtained for variant 3.

In a further variant 4 of the process according to the invention, the industrial measures of the preceding variants are brought together and combined.

In the simplest case, the extraction stages (2) and (3) are added and each is carried out in the manner described with a partial stream of (C) and a partial stream of (D), which in this case is divided into three partial streams.

It is more advantageous to use as organic phase (R) in extraction stage (2) a partial stream of the stream (P) containing a polyamine fraction which is more highly enriched in qualitative terms and less concentrated in quantitative terms.

In preference, variant 4 is carried out in such a way that a partial stream of (D) and/or preferably a partial stream of (P) is used as organic phase (R) in the extraction stage (2), and the aqueous phase (S) resulting in stage (2) is fed at least partially, preferably wholly to the extraction stage (3) and is used in (3) optionally with the addition of further aqueous phase from stream (C) and optionally auxiliary amine. In so doing, the organic phase (O) with its content of polyamine enriched in the same way is passed in counter-current to it in several stages with intimate mixing; optionally, the organic phase (O) is increased by the addition to (O) of a partial stream of the organic phase (T) resulting in the extraction stage (2).

As a result of said measures, a further increase in the qualitative enrichment effect is brought about in the organic phase (P) resulting in (3). In quantitative terms, said result may be achieved by metering and dividing up the streams with a relatively high, and hence favorable in energy terms, polyamine content in the phases resulting in (3), particularly in the organic phase (P).

The fact of combining the enrichment effect in (P) via the stream (R) as a partial stream of (P) and via the aqueous phase (S) has a self-intensifying effect.

As a result of the embodiment according to the invention and the inclusion of the extraction stages (2) to (4) in variant (4) with process criteria such as disproportionation instead of fractional extraction in stage (3), with self-intensification due to connection with extraction stage (2) and recovery of extraction agent in stage (2) without distillation for use in process stage (4) and optionally in (3), there results a maximum qualitative separating efficiency which, in combination with the variation in molarity of the aqueous phases in stages (2) to (4), leads to a wide field of application of the process according to the invention.

The invention is further illustrated but is not intended to be limited by the following examples in which all parts and percentages are by weight unless otherwise specified.

EXAMPLE

Starting polyamine mixture (A) (4,900 kg/h) is mixed with the stream (C) (19.307 kg/h) composed substantially of polyamine mixture, aniline, hydrogen chloride and water. Stream (C) is formed from streams (U) and (Q).

The resulting aqueous phase (streams A+C) has the following average composition

| Stream (A) + (C)<br>(24.207 kg/h) | 28.6% polyarylamine<br>18.9% aniline<br>5.8% hydrogen chloride<br>46.7% water |
|---|---| and is passed in counter-current to stream (B) in a multi-stage extractor (4) at 90° C., which stream (B) has the following composition:

| Stream (B)<br>(9.429 kg/h) | 29.7% aniline<br>69.2% xylene<br>approx. 1.1% water. |
|---|---|

The organic phase (D) leaving the extractor (4) is fed wholly to the extractor (3) and is in this case identical in terms of quantity and composition to stream (O). Stream (D) and (O) has the following average composition:

| Stream (D) and (O)<br>(12.106 kg/h) | 22.8% polyarylamine<br>22.3% aniline<br>53.9% xylene<br><0.1% hydrogen chloride<br>approx. 1.0% water. |
|---|---|

The aqueous phase (H) leaving the extractor (4) has the following average composition:

| Stream (H)<br>(21.530 kg/h) | 19.4% polyarylamine<br>21.7% aniline<br>6.5% hydrogen chloride<br>52.4% water. |
|---|---|

Stream (H) is combined with stream (Y) (approx. 2.9 kg/h) and passed in counter-current to the organic stream (J) in the multi-stage extractor (5) at 90° C.

| Stream (H) + (Y)<br>(24.441 kg/h)<br>Stream (J)<br>(21.958 kg/h) | 54.9% aniline<br>44.1 % xylene<br>approx. 1.0% water |
|---|---|

Stream (J) is formed from distillate stream (M) of the distillation stage (7.1) and a partial stream of (F).

The organic phase (L) leaving the extractor (5) is obtained with the following average composition:

| Stream (L) | 16.0% polyarylamine |
| --- | --- |
| (25.000 kg/h) | 44.1% aniline |
| | 38.8% xylene |
| | <0.1% hydrogen chloride |
| | approx. 1.0% water. |

Stream (L) is washed in counter-current with water (approx. 2 kg/h) in a washing stage (7.0) designed as a multi-stage extractor.

For safety, the washed stream (L) is washed with dilute sodium hydroxide solution. The aqueous phase is removed as waste water.

In the subsequent distillation stage (7.1), water, xylene and aniline are separated from the polyamine fraction (stream N) obtained as distillation bottom product.

The distillate obtained in distillation stage (7.1)—optionally after mechanical separation of the water separated when cooling the distillate—is combined as stream (M) with a partial stream of the stream (F) comprising substantially aniline from distillation stage (6.2) to form the stream (J) used as extraction agent in extraction stage (5).

The polyamine fraction (N) is collected in tank (10) as ortho-poor partial product in a quantity of approx. 4.0 kg/h.

The aqueous phase (K) leaving extractor (5) has the following average composition:

| Stream (K) | 0.8% polyarylamine |
| --- | --- |
| (21.399 kg/h) | 26.6% aniline |
| | 6.6% hydrogen chloride |
| | 66.0% water. |

Stream (K) is divided into a first partial stream which is concentrated in a water evaporator (8) by distillation of water (stream X: approx. 2.9 kg/h) and then fed as stream (U) to extraction stage (4),

| Stream (U) | 1.0% polyarylamine |
| --- | --- |
| (11.375 kg/h) | 33.3% aniline |
| | 8.2% hydrogen chloride |
| | 57.5% water | and a second partial stream which is fed directly, i.e. with the composition of stream (K), to extraction stage (3).

In the multi-stage extractor (3), the aqueous partial stream of (K) is passed in counter-current at 90° C. to an organic phase (O), in the present case identical to stream (D) in terms of quantity and composition.

The aqueous phase (Q) resulting in extractor (3) is combined with the aqueous phase (U) to form aqueous phase (C).

| Stream (Q) | 24.1% polyarylamine |
| --- | --- |
| (7.932 kg/h) | 10.0% aniline |
| | 5.9% hydrogen chloride |
| | 60.0% water. |

The organic phase (P) resulting in the extractor (3) has the following average composition:

| Stream (P) | 7.9% polyarylamine |
| --- | --- |
| (11.374 kg/h) | 33.6% aniline |
| | 57.4% xylene |
| | <0.1% hydrogen chloride |
| | approx. 1.0% water. |

In a washing stage (6.0) designed as a multi-stage extractor, the stream (P) is washed in counter-current with water from stream (X) (approx. 0.9 kg/h).

For safety, the washed stream (P) is washed with dilute sodium hydroxide solution. The aqueous phase is removed as waste water.

The washed stream (P) from which acid residues have been removed is freed in a first distillation stage (6.1) from the major part of the xylene and a part of the aniline. The distillate (stream (E)) is used to form stream (B).

In a second distillation stage (6.2), the aniline and residual xylene is distilled off from the bottom phase of (6.1). The distillate is divided into streams (B) and (J).

There remains as distillation bottom product from stage (6.2) a polyamine mixture which is collected as stream (G) at a rate of 0.90 kg/h in tank (9).

The acid quantities removed from the system via the safety neutralization stages during the wash with sodium hydroxide solution are replaced from outside by the addition of stream (C), and water quantities withdrawn are replaced by addition to stream (X).

| Polyarylamine GC: | A (wt. %) | G wt. %) | N (wt. %) |
| --- | --- | --- | --- |
| 2,2'-diaminodiphenylmethane | 0.22 | 1.20 | — |
| 2,4'-diaminodiphenylmethane | 7.12 | 35.20 | 0.80 |
| 4,4'-diaminodiphenylmethane | 60.20 | 26.40 | 67.80 |
| N-methyl-4,4'-diaminodiphenylmethane | 0.21 | 0.70 | 0.10 |
| Σ diaminodiphenylmethane | 67.74 | 63.50 | 68.70 |
| Σ polynuclear polyamines | 32.26 | 36.50 | 31.30 |
| Quantity distribution | 100% | 18.4% | 81.6% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the fractionation and purification of aromatic polyamine mixtures comprising:

a) mixing the polyamine starting mixture in a first extraction stage with a two-phase system comprising (i) a hydrophobic solvent phase which consists essentially of hydrophobic solvent and optionally an aromatic auxiliary amine which is substantially insoluble in water and exhibits at normal pressure a boiling point which is at least 20° C. below the boiling point of the lowest-boiling component of the starting mixture and at least 20° C. above the boiling point of the solvent, and optionally polyamine, and (ii) an aqueous phase consisting essentially of water, a strong acid and auxiliary amine present at least in part in the salt form, and optionally polyamines present at least in part in the salt form, with said first extraction stage operating on the countercurrent principle, and wherein said polyamine starting mixture is introduced into said first extraction stage with said aqueous phase, with a first aqueous phase and a first organic phase exiting said first extraction stage, b) distilling said first organic phase in a multi-stage distillation into i) a first fraction consisting essentially of hydrophobic solvent and optionally auxiliary amine, ii) a second fraction consisting essentially of auxiliary amine and optionally hydrophobic solvent, and iii) a distillation residue consisting essentially of a first polyamine fraction, c) extracting said first aqueous phase in a second extraction stage with a solvent phase consisting essentially of hydrophobic solvent and auxiliary amine, said second extraction stage operating on the countercurrent principle, with i) a second aqueous phase, said second aqueous phase being reduced in amine content and ii) a second organic phase exiting said second extraction stage, d) separating at least a portion of said second organic phase in a distillation stage into
  i) a first distillate consisting essentially of hydrophobic solvent and auxiliary amine, and
  ii) a distillation residue consisting essentially of a second polyamine fraction, e) recycling said second aqueous phase as at least a portion of said aqueous phase, and f) combining said first distillate with at least a portion of said second fraction to form at least a portion of said solvent phase.

2. A process for the fractionation and purification of aromatic polyamine mixtures wherein
  a) the polyamine starting mixture (A) is distributed in a two-phase system comprising (i) a hydrophobic solvent phase (B) which is composed substantially of hydrophobic solvent and optionally an aromatic auxiliary amine that is practically insoluble in water and under normal pressure has a boiling point at least 20° C. below the boiling point of the lowest boiling component of the starting mixture and at least 20° C. above the boiling point of the solvent, and optionally of polyamine, and (ii) an aqueous phase (C) comprising substantially water, a strong acid and auxiliary amine present at least partially in the salt form, and optionally polyamines present at least partially in the salt form, with the assistance of an extraction stage (4) operating on the counter-current principle with mixing of the phases, by introducing the starting polyamine mixture via the aqueous phase, into the extraction stage (4), and the organic phase (D) leaving the extraction stage (4) is separated
  b) optionally at least partially by means of an intermediate extraction stage (3) and/or
  c) optionally with separation of a partial stream before or after the extraction stage (3) optionally passed through, and return of the separated partial stream to the extraction stage (4) via an upstream extraction stage (2)
  d) in a multi-stage distillation (6.1), (6.2) into a first fraction (E), composed substantially of hydrophobic solvent and optionally auxiliary amine, a second fraction (F) composed substantially of auxiliary amine and optionally hydrophobic solvent and a distillation residue (G) composed substantially of a first polyamine fraction, and
  e) the aqueous phase (H) leaving the extraction stage (4) is fed to an extraction stage (5) in which an extraction of the aqueous phase takes place according to the principle of counter-current extraction with a solvent phase (J) comprising a solvent and auxiliary amine, and the aqueous phase (K) depleted in polyarylamine results, which is returned
  f) optionally at least partially via an intermediate distillation stage (8)
  g) optionally, at least partially via an intermediate extraction stage (3) and/or
  h) optionally at least partially, initially via an upstream extraction stage (2) and subsequently via an optionally present extraction stage (3)
  i) to the extraction stage (4) where it is used again as stream (C), optionally after the addition of water and/or auxiliary amine, and
  j) the organic phase (L) obtained in the extraction stage (5) is split into a distillate (M) comprising hydrophobic solvent and auxiliary amine and a distillation residue (N) comprising a second polyamine fraction, after which the distillate (M) is combined with at least a partial quantity of the distillate (F) obtained in the second distillation stage (6.2) of the organic phase (D) and is subsequently returned to the extraction stage (5) where it is used again.

3. The process of claim 2, wherein
  f) before being re-used, the aqueous phase (K) leaving the extraction stage (5) is freed at least partially from a part (X) of the water contained therein by distillation (8), said water being used optionally for washing (6.0) that part of the organic phase (D) leaving the extraction stage (4) and/or of the organic phase (P) leaving the extraction stage (3) fed to work-up by distillation (6.1), (6.2), and/or for washing (7.0) that part of the organic phase (L) leaving the extraction stage (5) fed to work-up by distillation (7.1) for the purpose of removing acid traces, the water (Y) obtained in so doing is returned to the aqueous phase at a suitable place and the resulting concentrated aqueous phase is combined with the optionally remaining residue of (K) and re-used as stream (C).

4. The process of claim 2, wherein
  b) the organic phase (D) obtained in the extraction stage (4) is extracted in counter-current at least partially in an intermediate extraction stage (3) with at least a partial quantity of stream (C) and/or is extracted in counter-current with at least a partial quantity of the aqueous phase obtained in the optionally present upstream extraction stage (2), the aqueous phase resulting in the intermediate extraction stage (3) is fed to the extraction stage (4) and the organic phase obtained in the intermediate extraction stage (3) is fed to the work-up stage (6).

5. The process of claim 2, wherein
  c) a partial stream of the organic phase (D) leaving the extraction stage (4) and/or a partial stream of the organic phase leaving the optionally present intermediate extraction stage (3) is separated, and extracted in counter-current in an upstream extraction stage (2) with a partial quantity, preferably with the entire quantity of the aqueous phase available as stream (C), the organic stream used in the extraction stage (2) is metered such that the most extensive transfer possible of the polyamine contained in the above-mentioned organic stream to the aqueous phase takes place in (2), the aqueous phase resulting in the upstream extraction stage (2) is fed to the extraction stage (3) optionally after the addition of water from stream (Y) and/or auxiliary amine, and the organic phase (T) obtained in the upstream extraction stage (2) and depleted in polyamine is fed to the extraction stage (4).

6. The process of claim 2, wherein the auxiliary amine used is aniline.

7. The process of claim 2, wherein the polyamine mixture used is a polyamine mixture of the diphenylmethane series obtained during acid-catalyses aniline-formaldehyde condensation.

8. In a process for the production of aromatic polyisocyanates by phosgenating an aromatic polyamine, the improvement wherein the aromatic polyamine is produced according to the process of claim 1.

9. In a process for the preparation of a cycloaliphatic polyamine by the hydrogenation of an aromatic polyamine, the improvement wherein the aromatic polyamine is produced according to the process of claim 1.

* * * * *